US00PP17575P2

(12) United States Plant Patent
Heins

(10) Patent No.: US PP17,575 P2
(45) Date of Patent: Apr. 3, 2007

(54) **VARIETY OF *BEGONIA* PLANT NAMED 'SOLENIA SUPER RED ORANGE'**

(50) Latin Name: ***Begonia elatior* hybrid [*Begonia*×*hiemalis***]
Varietal Denomination: Solenia Super Red Orange

(75) Inventor: Christiane Heins, Hann. Münden (DE)

(73) Assignee: Ernst Benary Samenzucht GmbH, Hann. Münden (DE)

( * ) Notice: Subject to any disclaimer, the term of this patent is extended or adjusted under 35 U.S.C. 154(b) by 0 days.

(21) Appl. No.: 11/369,242

(22) Filed: Mar. 7, 2006

(51) Int. Cl.
*A01H 5/00* (2006.01)

(52) U.S. Cl. ..... Plt./347

(58) Field of Classification Search ..... Plt./343, Plt./347
See application file for complete search history.

*Primary Examiner*—Anne Marie Grunberg
*Assistant Examiner*—S. B. McCormick-Ewoldt
(74) *Attorney, Agent, or Firm*—The Webb Law Firm

(57) ABSTRACT

A new and distinct *Begonia* plant having dark red flowers with orange undertones that exhibits good outdoor and garden performance.

2 Drawing Sheets

Botanical classification: *Begonia elatior* hybrid [*Begonia*×*hiemalis*].
Varietal denomination: 'Solenia Super Red Orange'.

BACKGROUND OF THE INVENTION

The present invention comprises a new and distinct cultivar of *Begonia* plant known by the varietal name 'Solenia Super Red Orange'. The new variety was discovered in 1998 in a selected breeding program in Gimte, Germany. The purpose of the breeding program was to develop a new variety with high sun and rain resistance, as well as good garden and outdoor performance. The new variety is the result of a cross between STS 97/R005 (female parent, unpatented) and TS 812 (male parent, unpatented). The new variety differs in flower color, form, habit and foliage characteristics from both parents. Specifically, the new variety is red-orange in color and its female parent is scarlet in color and its male parent is pink in color. The new variety has smooth foliage like its male parent, but the foliage of the new variety is darker green than both parents. Further, the foliage of its female parent is pubescent. The new variety also exhibits a compact, rounded growth habit, while its female parent has a strong growth habit. The new variety was first asexually reproduced in the winter 1998/1999 season by cuttings in Germany. The new variety has been trial and field tested in Germany and has been found to retain its distinctive characteristics and remain true to type through successive propagations.

The following traits distinguish 'Solenia Super Red Orange' as a new and distinct cultivar from other *begonia* varieties known to the breeder:

1. The flower color is dark red with orange undertones.
2. The new variety exhibits good outdoor and garden performance.

Further, the foliage of the new variety is Green Group 139A and has a shiny appearance, while the silky foliage of 'Solenia Red Improved' (unpatented) is green and brown on the upperside and reddish in color on the underside. Also, the flower color of the new variety is Red Group 44A, while the flower color of 'Solenia Red Improved' is Red Group 43B.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
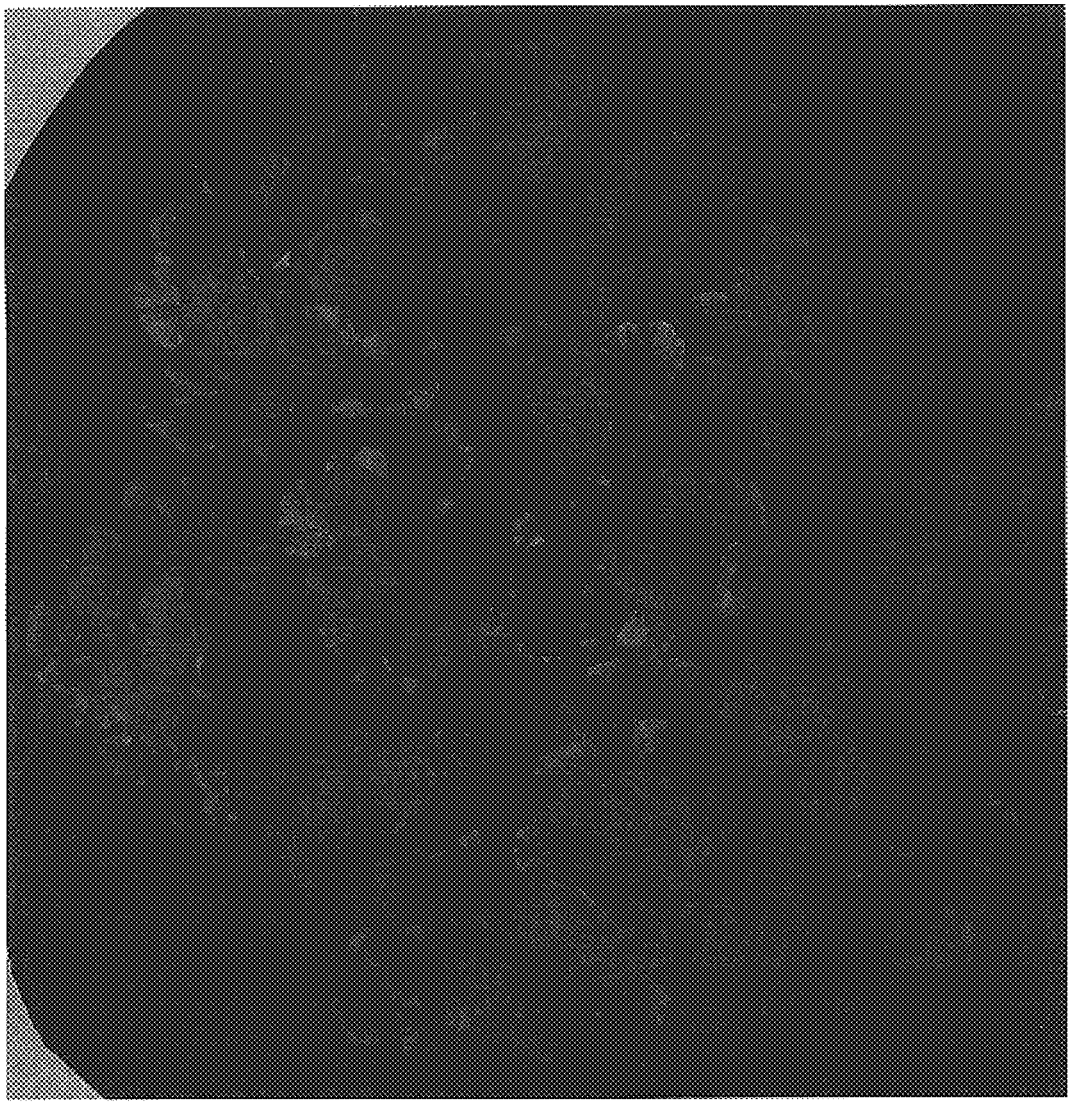
FIG. 1 is photograph of an entire plant of the new variety.
Figure 2:
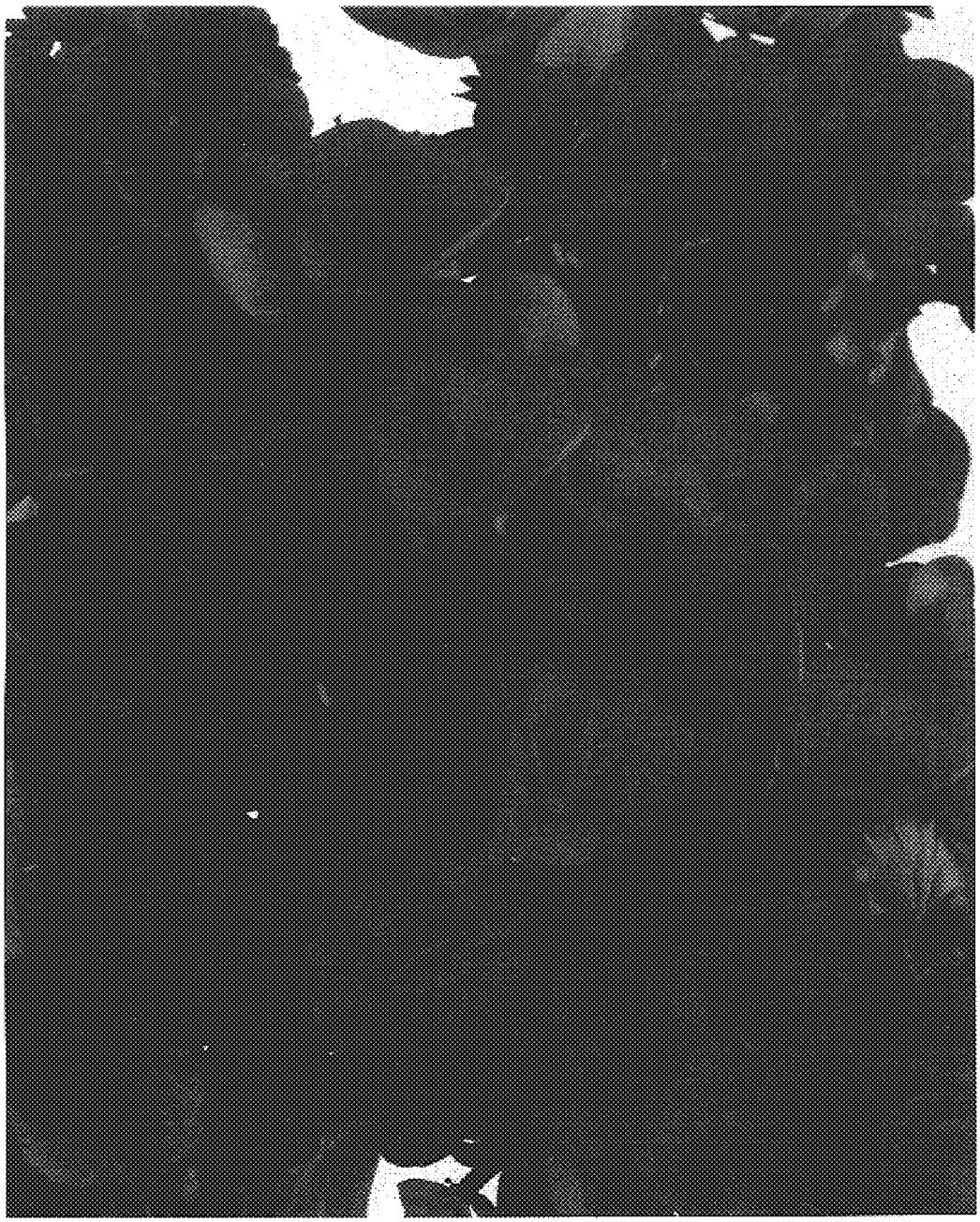
FIG. 2 is a close-up photograph of the flowers of the new variety.

The following detailed description sets forth characteristics of the new cultivar. The data which defines these characteristics were collected by asexual reproductions by cuttings carried out in Germany. The plants were exposed to an average temperature of 18° C. and 14 hours of long day light. Plants for the description were 6 months old and in 13 cm containers. The color readings were taken indoors under natural light. Color references are primarily to The R.H.S. Colour Chart of The Royal Horticultural Society of London.

PLANT

Form: Upright.
Time to initiate root development: Approximately three weeks.
Height (from soil to top of flowers): 9.45" (26 cm).
Plant diameter: 10.6" (27 cm).
Vigor: Good.
Branching habit: Medium.
Tubers: None present.
Lateral branches:
- *Color.*—Yellow-Green Group 146D with some brownish-red color present.
- *Texture.*—Smooth.
- *Length.*—5.9" (15 cm).
- *Diameter.*—5.5" (14 cm).
- *Internode length.*—0.8" (2 cm).
- *Quantity.*—4.

Foliage:

*Arrangement.*—Alternate.

*Number of leaves per stem.*—6.

*Size of leaf.*—Length: 4.7"–5.5" (12–14 cm). Width: 3.5"–3.9" (9–10 cm). Shape of leaf: Typical *Begonia* leaf-shape; kidney-shaped with an acute tip. Shape of apex: Acute.

*Shape of base.*—Oblique.

*Texture.*—Smooth, with venation present.

*Margin type.*—Bicrenate.

*Fragrance.*—None present.

*Color.*—Young leaves: Upper surface: Green Group 139A. Lower surface: Green Group 137A. Mature leaves: Upper surface: Green Group 139A. Lower surface: Green Group 137B.

*Petiole.*—Length: 1.57" (4 cm). Diameter: 0.12" (0.3 cm). Color: Yellow-Green Group 146D with a reddish gleam. Texture: Smooth.

*Veins.*—Venation pattern: Star-shaped. Color: Upper surface: Green Group 137C. Lower surface: Green Group 137D.

FLOWER

Natural flowering season: May/June in Germany.

Flower habit: Double flowering.

Number of flowers per plant: 70–90.

Time of day of flower opening: Flowers are always open.

Longevity: 2 to 3 weeks on the plant.

Flower height: 0.6" (1.5 cm).

Flower diameter: 1.38" (3.5 cm).

Bud:

*Stage of development when described.*—At the beginning of opening.

*Shape.*—Semi-circle.

*Diameter.*—0.6" (1.5 cm).

*Length.*—0.8" (2 cm).

*Color.*—Red Group 44A.

Petals:

*Arrangement.*—Double.

*Quantity.*—20–25 per flower.

*Length.*—0.98" (2.5 cm).

*Width.*—0.8" (2 cm).

*Shape.*—Semi-circle.

*Apex.*—Round.

*Base.*—Straight.

*Margin.*—Entire.

*Texture.*—Smooth.

*Color.*—When opening: Red Group 44A. Fully opened: Red Group 44A.

Peduncles:

*Length.*—2.76"–3.15" (7–8 cm).

*Diameter.*—0.16" (0.4 cm).

*Color.*—Yellow-Green Group 152B with a reddish tinge.

*Texture.*—Smooth.

*Orientation.*—Upright.

*Strength.*—Strong.

Pedicels:

*Length.*—0.39" (1 cm).

*Width.*—0.04" (0.1 cm).

*Color.*—Greyed-Orange Group 172C with a reddish tinge.

*Strength.*—Medium.

*Orientation.*—Angled.

Reproductive organs: None present.

Seed production: None.

Disease resistance: No unusual susceptibility noticed to date.

Weather tolerance: Good; from 12–35° C. (54° F.–95° F.).

Female/male flowers: Only 2–3 female (single flowers) are present per plant. All other flowers are male (fully filled flowers).

I claim:

1. A new and distinct variety of *Begonia* plant substantially as shown and described.

* * * * *